US005641930A

United States Patent [19]

Nakada et al.

[11] Patent Number: 5,641,930

[45] Date of Patent: Jun. 24, 1997

[54] ELECTRONIC MUSICAL APPARATUS FOR CONTROLLING MUSICAL TONE USING INITIAL TOUCH INFORMATION

[75] Inventors: Akira Nakada; Takeo Shibukawa; Yasuhiro Hinago, all of Hamamatsu, Japan

[73] Assignee: Yamaha Corporation, Japan

[21] Appl. No.: 375,857

[22] Filed: Jan. 20, 1995

[30] Foreign Application Priority Data

Jan. 21, 1994 [JP] Japan .................................... 6-022011

[51] Int. Cl.$^{6}$ ................................ G01P 3/00; G16H 5/00

[52] U.S. Cl. ................................ 84/658; 84/737; 84/745; 84/DIG. 7

[58] Field of Search ..................... 84/737, 738, 743–745, 84/658, 687, DIG. 7

[56] References Cited

U.S. PATENT DOCUMENTS

| | | | |
|---|---|---|---|
| 4,018,125 | 4/1977 | Nishimoto | 84/658 X |
| 4,109,208 | 8/1978 | Tomisawa et al. | 328/13 |
| 4,111,091 | 9/1978 | Hinago | 84/687 |
| 4,665,788 | 5/1987 | Tripp et al. | 84/687 X |
| 4,979,423 | 12/1990 | Watanabe | 84/690 |
| 5,025,705 | 6/1991 | Raskin | 84/745 X |
| 5,428,185 | 6/1995 | Kunimoto et al. | 84/658 |
| 5,498,836 | 3/1996 | Okamoto et al. | 84/658 |

FOREIGN PATENT DOCUMENTS 59-105692 6/1984 Japan .

*Primary Examiner*—David S. Martin
*Assistant Examiner*—Jeffrey W. Donels
*Attorney, Agent, or Firm*—Graham & James LLP

[57] ABSTRACT

An electronic musical instrument comprises a plurality of keys being displaceable relative to a support member therefor in response to depression thereof. A CPU detects velocity of depression of each of the keys from displacement of the each key caused by depression thereof, and also detects a pressure force or an impact force with which the each key urgingly contacts a stationary member at or near termination of depression of the each key. The CPU is responsive to the detected velocity of depression and pressure force or impact force, for determining initial touch information for a musical tone to be generated or at least one musical tone parameter, and for controlling the musical tone to be generated, based on the determined initial touch information.

6 Claims, 12 Drawing Sheets

| FIG.7 | |
|---|---|
| FIG.7A | FIG.7B |

| | | | |
|---|---|---|---|
| 1 | KEY DATA KD1 | 1 | TIME DATA (t1(1)) |
| 2 | KEY DATA KD2 | 1 | TIME DATA (t1(2)) |
| 3 | KEY DATA KD3 | 0 | TIME DATA (t1(3)) |
| ⋮ | ⋮ | ⋮ | ⋮ |

FIG.10

| | | | | | |
|---|---|---|---|---|---|
| 1 | KEY DATA KD1 | 1 | TIME DATA (t2(1)) | \|t1(1)—t2(1)\| | Pr(1) |
| 2 | KEY DATA KD2 | 1 | TIME DATA (t2(2)) | \|t1(2)—t2(2)\| | Pr(2) |
| 3 | KEY DATA KD4 | 0 | TIME DATA (t2(3)) | | |
| ..... | ..... | ..... | ..... | ..... | ..... |

ELECTRONIC MUSICAL APPARATUS FOR CONTROLLING MUSICAL TONE USING INITIAL TOUCH INFORMATION

BACKGROUND OF THE INVENTION

1. Field of the Invention

This invention relates to an electronic musical instrument which has a keyboard device capable of expressing sounds having wide dynamic ranges.

2. Prior Art

As an electronic musical instrument of this kind, there has been conventionally well known one which has two or more switches which are disposed to be closed at different times (hereinafter referred to as "contact times") from each other when a corresponding key is depressed, and detects the difference between the contact times to calculate therefrom the velocity of depression of the key (hereinafter referred to as "key depression velocity") to thereby realize a sound having a dynamic range corresponding to the calculated key depression velocity, i.e. the key depression strength.

However, according to the above conventional electronic musical instrument, it is difficult to accurately detect values of the key depression strength larger than f (forte).

More specifically, referring to FIG. 1 showing a characteristic curve representing the relationship between the key depression strength and the contact time difference, the characteristic curve has a sharp gradient relative to the time difference in a key depression strength region less than f (forte) so that the key depression strength can be easily determined from the contact time difference, whereas the curve has a gentle gradient in a key depression strength region larger than f (forte) so that the key depression strength cannot be easily accurately determined from the contact time difference due to a small change in the contact time difference relative to a change in the key depression strength. As a result, it is difficult to express a sound from values of the key depression strength exceeding f (forte).

SUMMARY OF THE INVENTION

It is an object of the invention to provide an electronic musical instrument which is capable of expressing sounds having wide dynamic ranges from ppp (pianissimo) to fff (fortessimo).

To attain the object, the present invention provides an electronic musical instrument comprising a plurality of keys, a support member supporting the key, said keys being displaceable relative to the support member in response to depression thereof, key depression velocity-detecting means for detecting velocity of depression of each of the keys from displacement of the each key caused by depression thereof, a stationary member, force detecting means for detecting a pressure force or an impact force with which the each key urgingly contacts the stationary member at or near termination of depression of the each key, and initial touch information-determining means responsive to the velocity of depression detected by the key depression velocity-detecting means and the pressure force or the impact force detected by the force detecting means, for determining initial touch information for a musical tone to be generated or at least one musical tone parameter, and for controlling the musical tone to be generated, based on the determined initial touch information.

Preferably, the stationary member is the support member.

In another form of the invention, the electronic musical instrument comprises a plurality of keys, a support member supporting the key, said keys being displaceable relative to the support member in response to depression thereof, key depression velocity-detecting means for detecting velocity of depression of each of the keys from displacement of the each key caused by depression thereof, a moving member being movable in unison with the each key in response to depression thereof, a stationary member, force detecting means for detecting a pressure force or an impact force with which the moving member urgingly contacts the stationary member at or near termination of depression of the each key, and initial touch information-determining means responsive to the velocity of depression detected by the key depression velocity-detecting means and the pressure force or the impact force detected by the force detecting means, for determining initial touch information for a musical tone to be generated or at least one musical tone parameter, and for controlling the musical tone to be generated, based on the determined initial touch information.

Preferably, the moving member is a mass element having a predetermined amount of mass.

Also preferably, the stationary member is the support member.

Advantageously, the initial touch information-determining means controls the musical tone to be generated or the at least one musical tone parameter according to the velocity of depression detected by the depression velocity-detecting means if the detected velocity of depression is below a predetermined value, the initial touch information-determining means determining the initial touch information for the musical tone to be generated or the at least one musical tone parameter according to the detected velocity of depression and the force detected by the force detecting means.

The above and other objects, features, and advantages of the invention will be more apparent from the following detailed description taken in conjunction with the accompanying drawings.

BRIEF DESCRIPTION OF THE DRAWINGS

FIG. 5 (*b*) is a diagram three-dimensionally expressing the structure of the table TBL(v,p);

FIG. 7 is a flowchart showing details of a subroutine for keyboard processing executed at a step S2 in FIG. 6;

FIG. 10 is a diagram showing part of a memory map in a memory buffer KBUF2;

DETAILED DESCRIPTION

The invention will now be described in detail with reference to the drawings showing preferred embodiments thereof.

Figure 2:
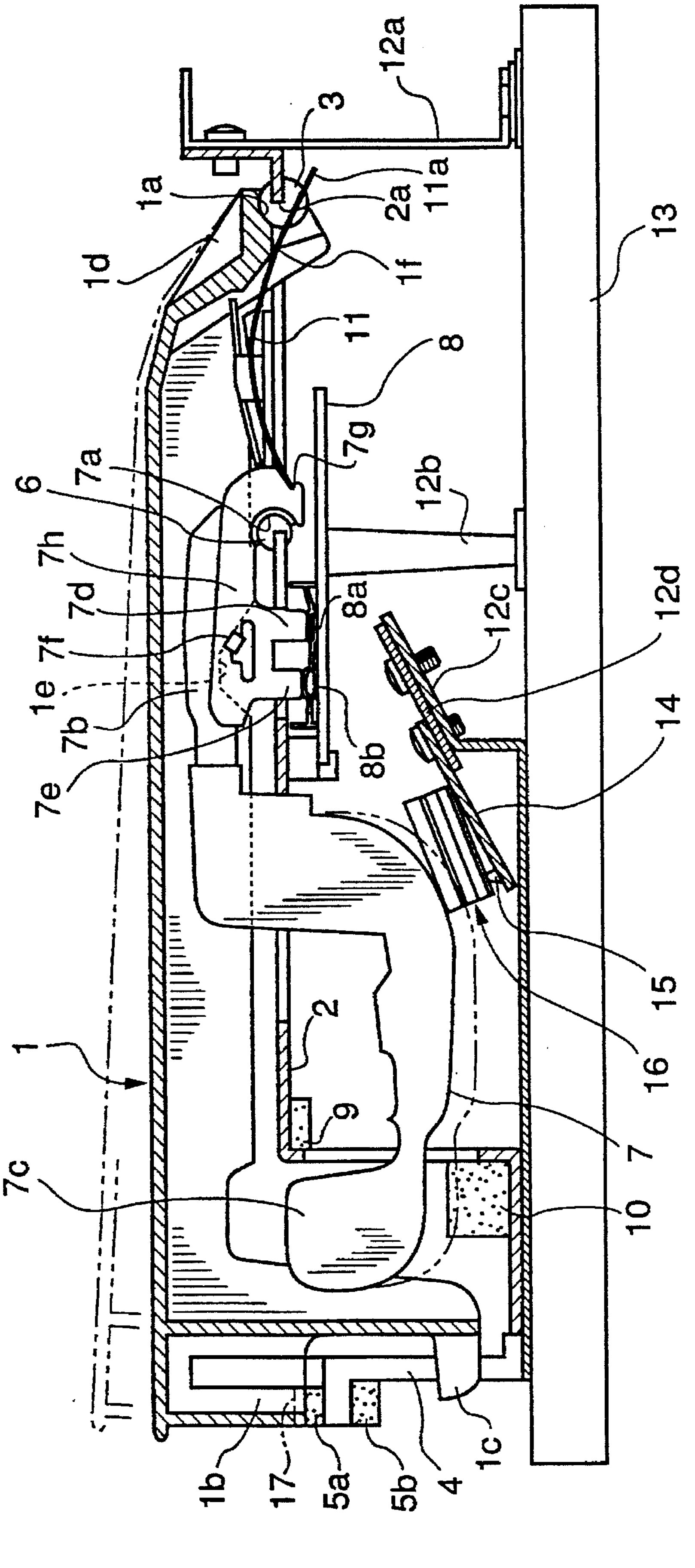
FIG. 2 is a longitudinal sectional view showing the construction of a keyboard of an electronic musical instrument according to an embodiment of the invention.

Referring first to FIG. 2, there is shown a longitudinal section of the construction of a keyboard of an electronic musical instrument according to an embodiment of the invention.

In the figure, reference numeral 1 designates a key (white key) which is formed of a one-piece resin material and has a generally inverted U-shaped cross section with a bottom surface being open. The key 1 has a recess 1*a* formed at a rear end thereof and having a cylindrical inner surface to serve as a fulcrum for the key. The key 1 is supported for vertically swinging movement by a keyboard frame (hereinafter referred to merely as "the frame") 2 formed of a plate-like member as a support member for the key, by means of a support pin 3 with a circular cross section fixed to the frame 2. The recess 1*a* of the key 1 is engaged on the support pin 3 such that the key 1 can be swung about the pin 3. The support pin 3 is formed by "outsert" formation on a rear edge of a rectangular slit 2*a* formed in the frame 2.

At a front end portion of the key 1, stoppers 1*b* and 1*c* downwardly pendent integrally from opposite lateral walls of the key 1 are disposed to abut respectively against an upper limit stopper 5*a* and a lower limit stopper 5*b* attached to horizontal surfaces of a key guide 4 erected on a front end portion of the frame 2 to thereby determine the swinging range of the key 1.

A support pin 6 is formed by "outsert" formation integrally on a front edge of the slit 2*a* of the frame 2 and on which a recess 7*a* of a hammer 7 as a mass element is engaged such that the hammer 7 can be swung about the pin 6 which forms a second fulcrum (fulcrum for the mass element). The hammer 7 has a core 7*b* formed of a metal piece and having such a weight that the whole hammer 7 has a predetermined weight. The hammer 7 has a front half portion thereof coated with a resin material by "outsert" formation such that its center of gravity lies at a front end 7*c* thereof.

A bifurcated protuberance with pushing arms 7*d* and 7*e* projects downwardly from the hammer 7 at a location close to the support pin 6 forming a hammer fulcrum. Above the arms 7*d*, 7*e*, protuberances 7*f* and 7*f* project from an outsert member 7*h* at opposite lateral sides of the core 7*b* such that recesses 1*e* and 1*e* formed in opposite lateral sides of the key 1 push the protuberances 7*f*, 7*f* to cause pivoting of the hammer 7 in a counterclockwise direction as viewed in the figure. As the hammer 7 thus pivots, the switch pushing arms 7*d*, 7*e* move downward to turn on a switch 8*a* of 1-make type and a switch 8*b* of 2-make type arranged on a base 8 secured on the frame 7, respectively, to cause generation of a musical tone-generating signal. An upper limit stopper 9 and a lower limit stopper 10 are attached, respectively, on upper and lower surfaces of the frame 2 to determine the swinging range of the hammer 7 in the clockwise direction.

A plate spring 11, which is formed with a fitting holder 11*a*, is supportedly engaged between a holder section if formed at a lower surface of a rear end portion 1*d* of the key 1 and an engaging groove 7*g* formed in the hammer 7 in a fashion extending rearwardly of the key 1. The plate spring 11 urges the key 1 in the clockwise direction to urge the recess 1*a* of the key 1 against the support pin 3, and at the same time urges the hammer 7 in the clockwise direction to urge the recess 7*a* of the hammer 7 against the support pin 6.

The frame 2 is supportedly secured on a horizontal shelf-like member 13 by means of stays 12*a* and 12*b*. A base member 14 formed of a high elasticity material is mounted on the shelf-like member 13 in an inclined fashion by means of a pressure sensor-holding stay 12*c* and a reinforcement plate 12*d*. A stress-concentrated member 15 formed of a hard material in the form of a needle or a hook is arranged on an upper surface of a front end of the base member 14. A pressure sensor 16 with a cushion member, not shown, contained therein has a front end thereof supported on the stress-concentrated member 15 while abutting on a base end portion of the base member 14, at such a location that the hammer 7 can be brought into urging contact with the pressure sensor 16.

The above description refers to the structure of a white key and its associated parts. The structure of black keys and their associated parts is substantially identical with the structure of white keys and their associated parts described above, description of which is therefore omitted.

When one of keys of the keyboard of the present embodiment constructed as above is depressed by the player, contacts of the 1-make type switch 8*a* are closed, followed by closing of contacts of the 2-make type switch 8*b*. Further, on this occasion output voltage from the pressure sensor 16 varies depending upon the strength of depression of the key. The pressure sensor 16 may be an electric resistance-variable type that the output value varies substantially in proportion to vertical pressure vertically applied to the sensor, or an impact sensor using a piezoelectric element which provides an output value which is a timewise differential value of vertical pressure applied to the sensor. In the case where the pressure sensor 16 uses a piezoelectric element, advantageously voltage from the sensor should be detected via an interface circuit such as a peak-hold circuit.

Although in the present embodiment the pressure sensor 16 is arranged for urging contact with a lower surface of a central portion of the hammer 7, this is not limitative, but the sensor may be arranged on the lower limit stopper 5*a* (corrugated section 17) of the key 1 in FIG. 2, or on the lower limit stopper 10 under a lower surface of a front end portion of the hammer 7.

Figure 3:
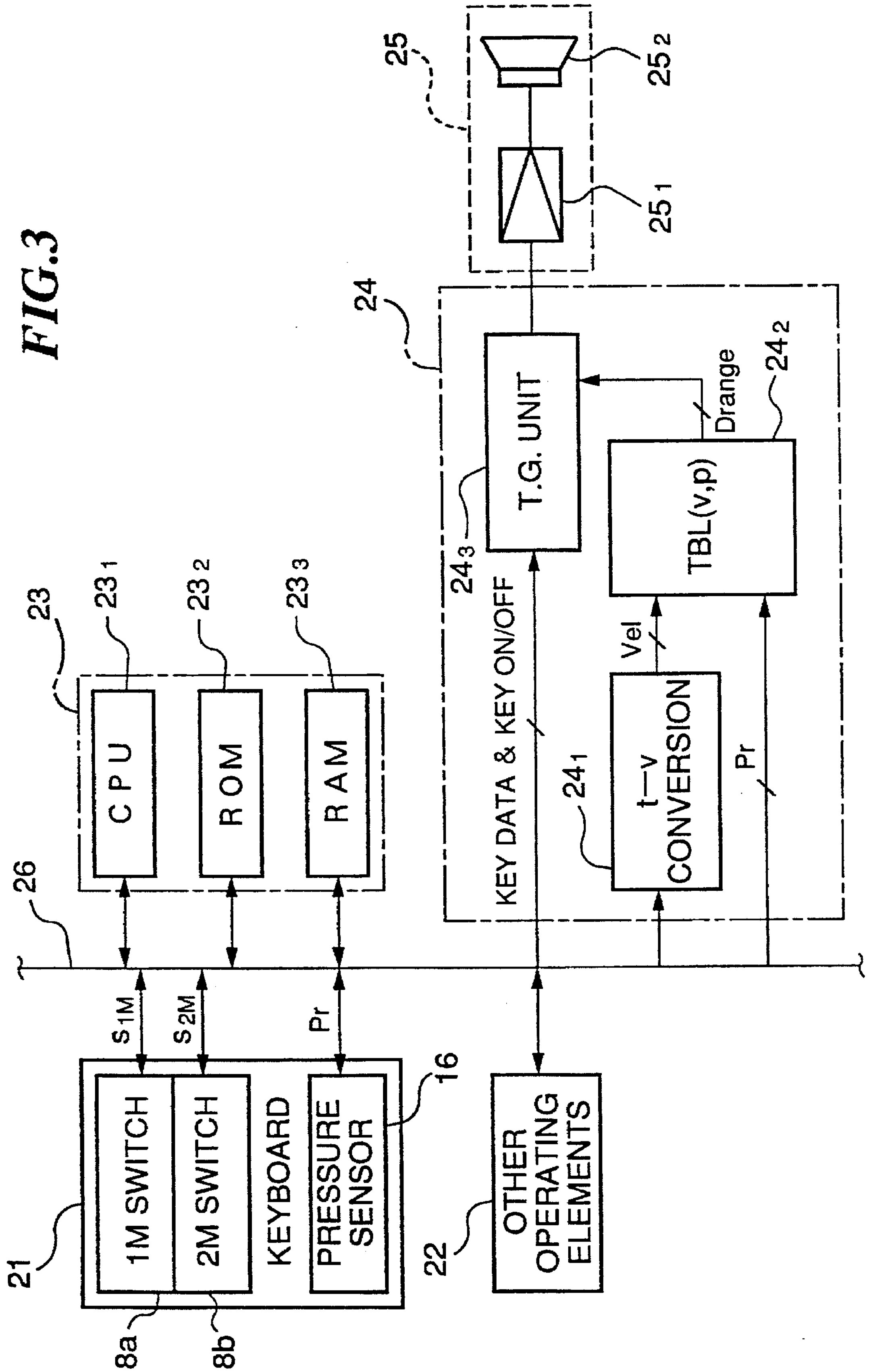
FIG. 3 is a block diagram schematically showing the electronic system arrangement of the electric musical instrument.

FIG. 3 schematically shows the electronic system arrangement of the electronic musical instrument according to the embodiment.

The electronic musical instrument is comprised of the keyboard 21 described above, other operating elements 22 for inputting other operating information, a microcomputer 23 for controlling the whole instrument, a tone generation block 24 for generating musical tone signals, and a sound system 25 for converting the musical tone signals into musical tones. These elements 21 to 24 are connected to each other via a bus 26, with an output of the tone generation block 24 being connected to an input of the sound system 25.

As previously mentioned, outputs from the keyboard 21, i.e. respective outputs from the 1-make type switch 8*a*, 2-make type switch 8*b*, and pressure sensor 16 are delivered to the bus as signals $s_1M$, $s_2M$, and Pr, respectively.

The microcomputer 23 is comprised of a CPU $\mathbf{23}_1$ for carrying out an operation, a ROM $\mathbf{23}_2$ storing control programs, table data, etc. used in the operation carried out by the CPU $\mathbf{23}_1$, and a RAM $\mathbf{23}_3$ for temporarily storing results of calculations, various input information, etc. used in the operation carried out by the CPU $\mathbf{23}_1$.

The tone generation block 24 is comprised of a t-v conversion table $\mathbf{24}_1$ for converting contact time difference data into a key depression velocity signal Vel, the contact time difference data being obtained from time data from the 1-make type switch 8*a* and the 2-make type switch 8*b* by the microcomputer 23, a table TBL(v,p) $\mathbf{24}_2$ for reading out a value Drange (dynamic range value) of strength of key depression from among values 0 to 127, based on the output signal Pr from the pressure sensor 16 and the key depression velocity signal Vel from the t-v conversion table $\mathbf{24}_1$, and a tone generation unit $\mathbf{24}_3$ for generating a musical tone signal based on the value Drange read from the table TBL(v,p) $\mathbf{24}_2$ and key data and a key on/off signal outputted by the CPU $\mathbf{23}_1$ in response to depression of the key 21. The contact time difference data is detected by reading count values of a so-called free-run counter for counting up a soft timer counter area preset in the RAM $\mathbf{23}_3$ by an interrupt processing or the like, respectively, when the 1-make type switch 8*a* and the 2-make type switch 8*b* become closed, and calculating a difference between the thus read count values. Further, in the present embodiment the contact time difference data and the output signal Pr from the pressure sensor 16 are each formed of 7 bits, and accordingly values Drange read from the table TBL(v,p) $\mathbf{24}_2$ are formed of 7 bits.

The sound system 25 is comprised of an amplifier $\mathbf{25}_1$ for amplifying a musical tone signal from the tone generation unit $\mathbf{24}_3$, and a loudspeaker $\mathbf{25}_2$ for converting the musical tone signal from the amplifier $\mathbf{25}_1$ into musical tones.

Figure 4:
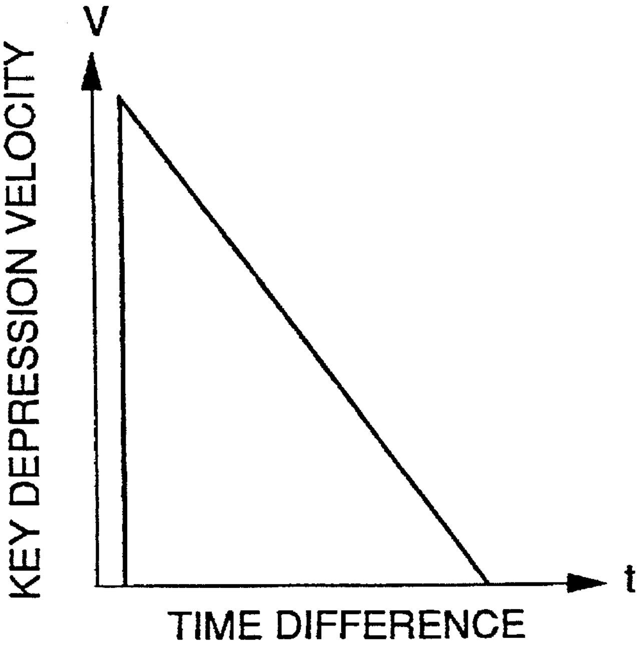
FIG. 4 is a diagram showing the relationship between key depression velocity and a time difference set in a t-v conversion table appearing in FIG. 3.

FIG. 4 shows the relationship between key depression velocity and a time difference set in the t-v conversion table TBL(v,p) $\mathbf{24}_2$. In the figure, the ordinate represents the key depression velocity, and the abscissa the time difference between the contact times of the 1-make type switch 8*a* and the 2-make type switch 8*b*. It is to be noted that in the figure a value of "0" is read out from the t-v conversion table $\mathbf{24}_1$ when the time difference is "0" or in the vicinity of "0". This is because generation of a musical tone signal is inhibited as occurrence of an error when data indicative of an excessively small time difference is generated.

Figure 5A:
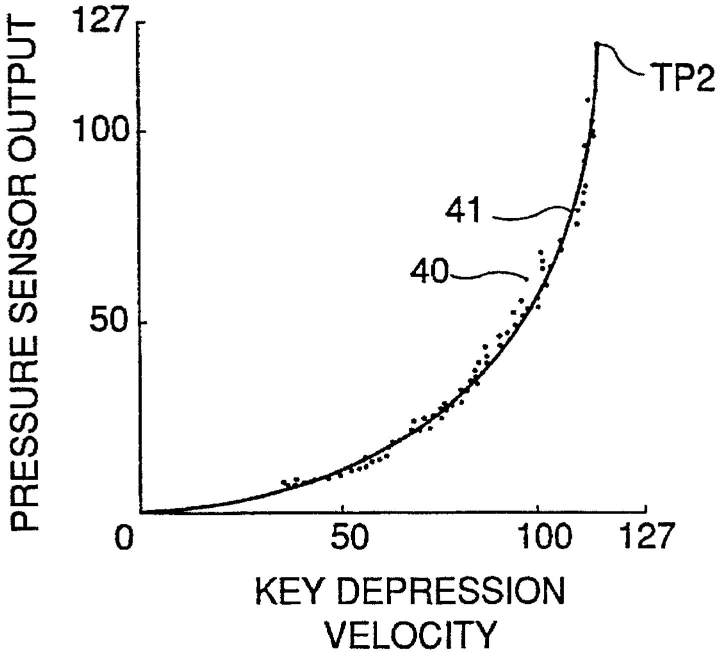
FIG. 5 (*a*) is a diagram showing the relationship between an output from a pressure sensor appearing in FIG. 2 and key depression velocity on which a table TBL(v,p) appearing in FIG. 3 is based.
Figure 5B:
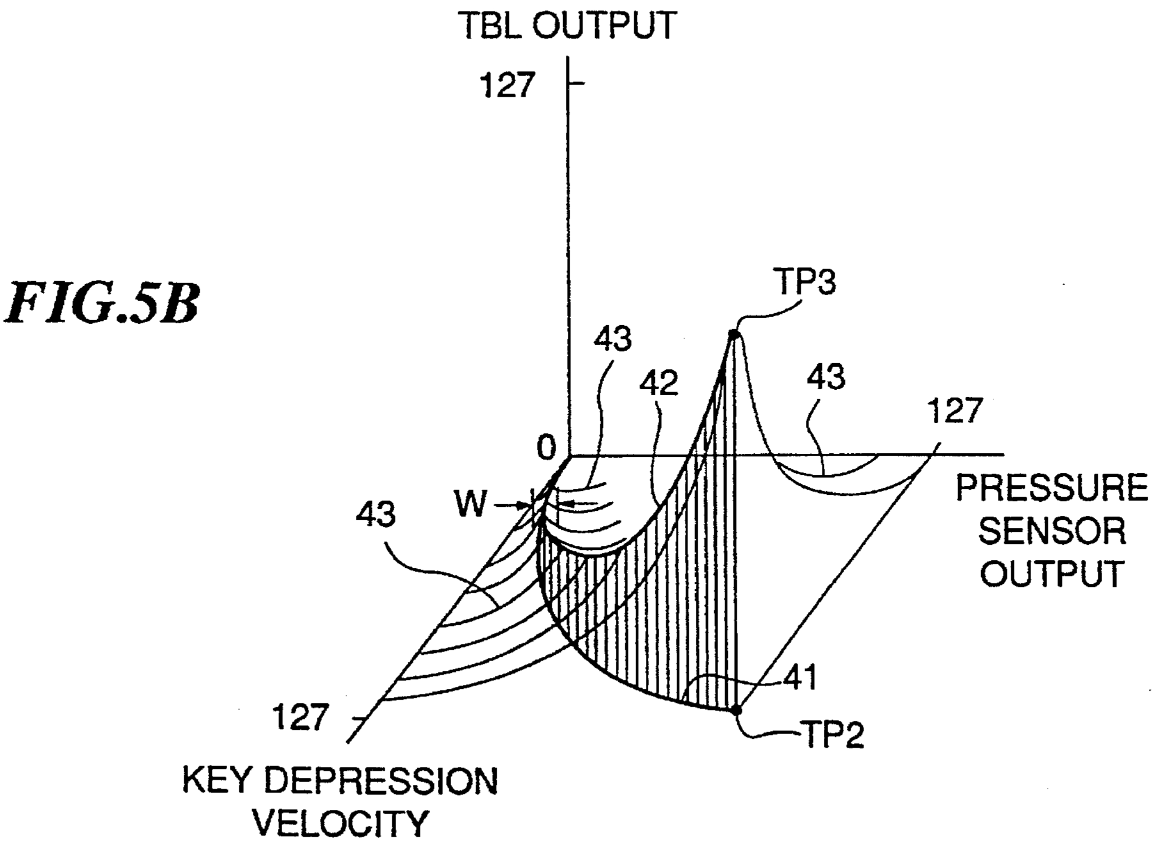

FIGS. 5 (*a*) and 5 (*b*) show, respectively, the relationship between the output from the pressure sensor 16 and key depression velocity on which the table TBL(v,p) $\mathbf{24}_2$ is based, and a three-dimensional representation of the structure of the table TBL(v,p) $\mathbf{24}_2$. In FIG. 5 (*a*), the ordinate represents the output from the pressure sensor 16 and the abscissa the output, i.e. key depression velocity, from the t-v conversion table $\mathbf{24}_1$ in FIG. 4. As shown in the figure, the t-v conversion table $\mathbf{24}_1$ is set such that one of values 0 to 127 is allotted to each data item (each dot along a characteristic curve 41), and one of the values 0 to 127 is selectively read out based on the key depression velocity and the output from the pressure sensor 16. As will be learned from FIG. 5 (*b*), if a key is depressed at a predetermined depression velocity, a predetermined output is obtained from the sensor 16 immediately after the key urgingly contacts the sensor, and a predetermined one of the values 0 to 127 is read out based on these two kinds of data. This relationship can be expressed as the table output value having an almost linearly increasing characteristic (almost looking like a right-angled triangle) of a plane as viewed from the front, the plane being projected from a curved surface extending through points 0, TP2 and TP3 and including a curved line 41. Three-dimensionally, a characteristic is obtained which has a mountain-like section with its ridge line formed by a main characteristic curve 42 corresponding to the table output value.

Figure 1:
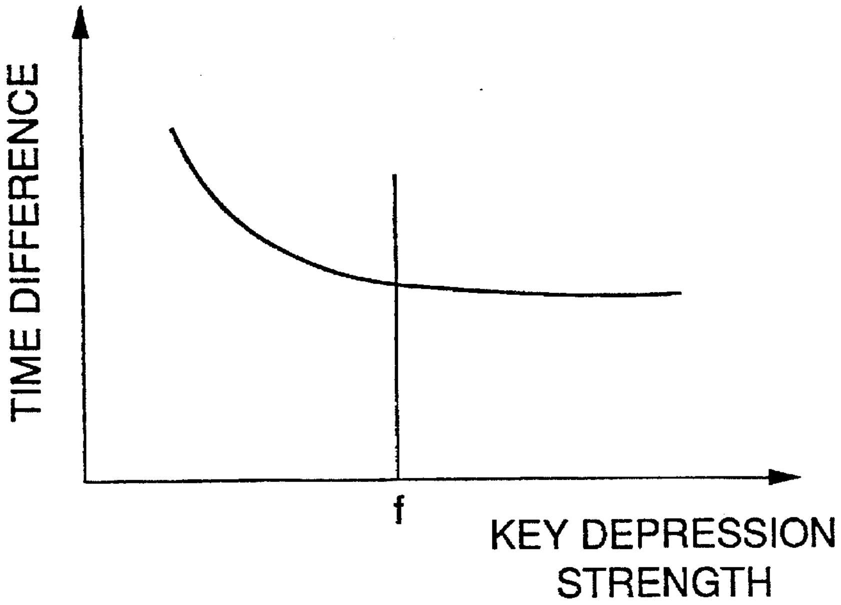
FIG. 1 is a diagram showing the relationship between key depression strength and a difference between contact times.

The reason why generation of musical tones is controlled by the use of the three-dimensional table will now be described. As mentioned previously with reference to FIG. 1, in the conventional electronic musical instrument which detects the key depression strength only from the difference between contact times of a plurality of switches, a large change in the time difference between contact times of the switches 8*a*, 8*b* cannot be obtained even if the key depression strength changes above f (forte) (unless special measures are taken, e.g. the key is struck by the hammer, or the key stroke is designed to have several times as large as a usual one). However, in the present embodiment, as shown in FIG. 2, the pressure sensor 16 is so arranged as to be urged or pressed by the hammer 17 near the termination of depression of the key 1. As a result, even when the key depression strength exceeds f (forte), the output from the pressure sensor 16 largely changes relative to a change in the key depression velocity, i.e. key depression strength, as clearly shown in FIG. 5 (*a*), even though the change in the contact time difference from the switches 8*a*, 8*b* is small relative to a change in the key depression strength.

In FIG. 5 (*a*), dots 40 were obtained by measuring approximately 100 times output values from the pressure sensor 16 obtained when the keyboard in FIG. 2 is operated with various key depression speeds. It was found that the distribution of dots thus obtained formed a certain curve 41. As is learned from the figure, the key depression velocity (speed) and the output from the pressure sensor 16 are in a particular correlation represented by the curve 41. Exactly observed, the dot distribution has a small dispersion. To allow tolerances corresponding to the dispersion, a foot section 43 is provided as shown in FIG. 5 (*b*). The foot section 43 may be omitted except a predetermined small width W lying about the ridge line 42. Since the test data in FIG. 5 (*a*) presents the above-mentioned strong correlation, such omission is possible, enabling reduction of the memory capacity.

The value obtained by reading from the table TBL(v,p) $\mathbf{24}_2$ (hereinafter referred to as "the table output value") is used in the present embodiment as data indicative of the dynamic range of musical tones to be generated.

However, the table output value may be used for tone color control including effect control, as well as or alternatively of dynamic range control. For example, the table output value may be used to control the cut-off frequencies of a low-pass filter, a band-pass filter, a high-pass filter, etc. In such an alternative case, if it is so set, e.g. in a low-pass filter that the larger the table output value, the higher the cut-off frequency, a musical tone abundant in bass and having depth can be obtained by depressing the key with a strong touch. Further, it may be also set such that the larger the table output value, the larger the reverberation depth. Further, the vibrato depth, vibrato speed, tremolo depth, tremolo speed, PAN, etc. may be similarly controlled.

By making the table output value corresponding to the dynamic range of musical tones to be generated, it is possible to easily express various changes in the musical tone generated, even if the key depression strength exceeds f (forte), as is distinct from the conventional electronic musical instrument. Even by making the table output value corresponding to other musical tone elements, similar excellent results can be obtained. Thus, by employing this technique, the capacity for musical expression in performance can be remarkably increased as compared with the prior art.

The control processing carried out by the CPU $23_1$ of the electronic musical instrument according to the invention constructed as above will now be described with reference to FIGS. 6 to 8.

Figure 6:
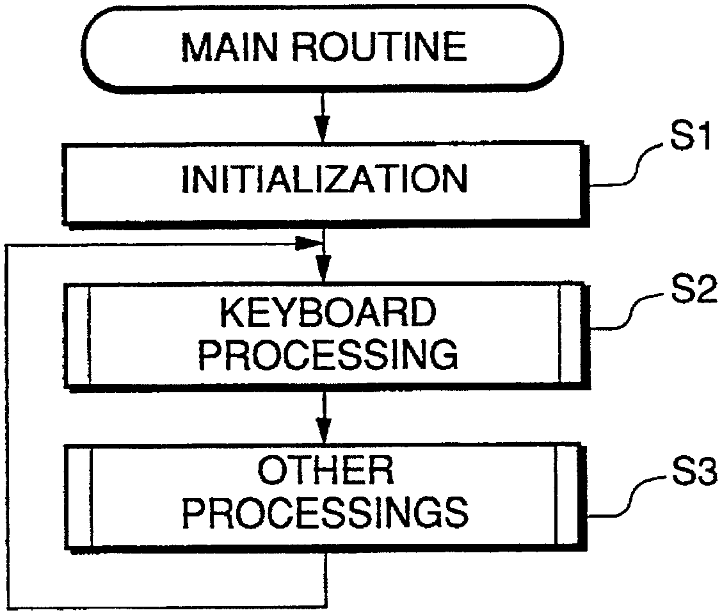
FIG. 6 is a flowchart showing a main routine executed by the electronic musical instrument.

FIG. 6 shows a flowchart of a main routine executed by the CPU $23_1$.

First, an initialization processing is carried out to carry out various initial settings at a step S1. Then, a keyboard processing, hereinafter described, and other processings are carried out, respectively, at steps S2 and S3, followed by the program returning to the step S2 to repeatedly execute the steps S2 and S3.

Figure 7A:
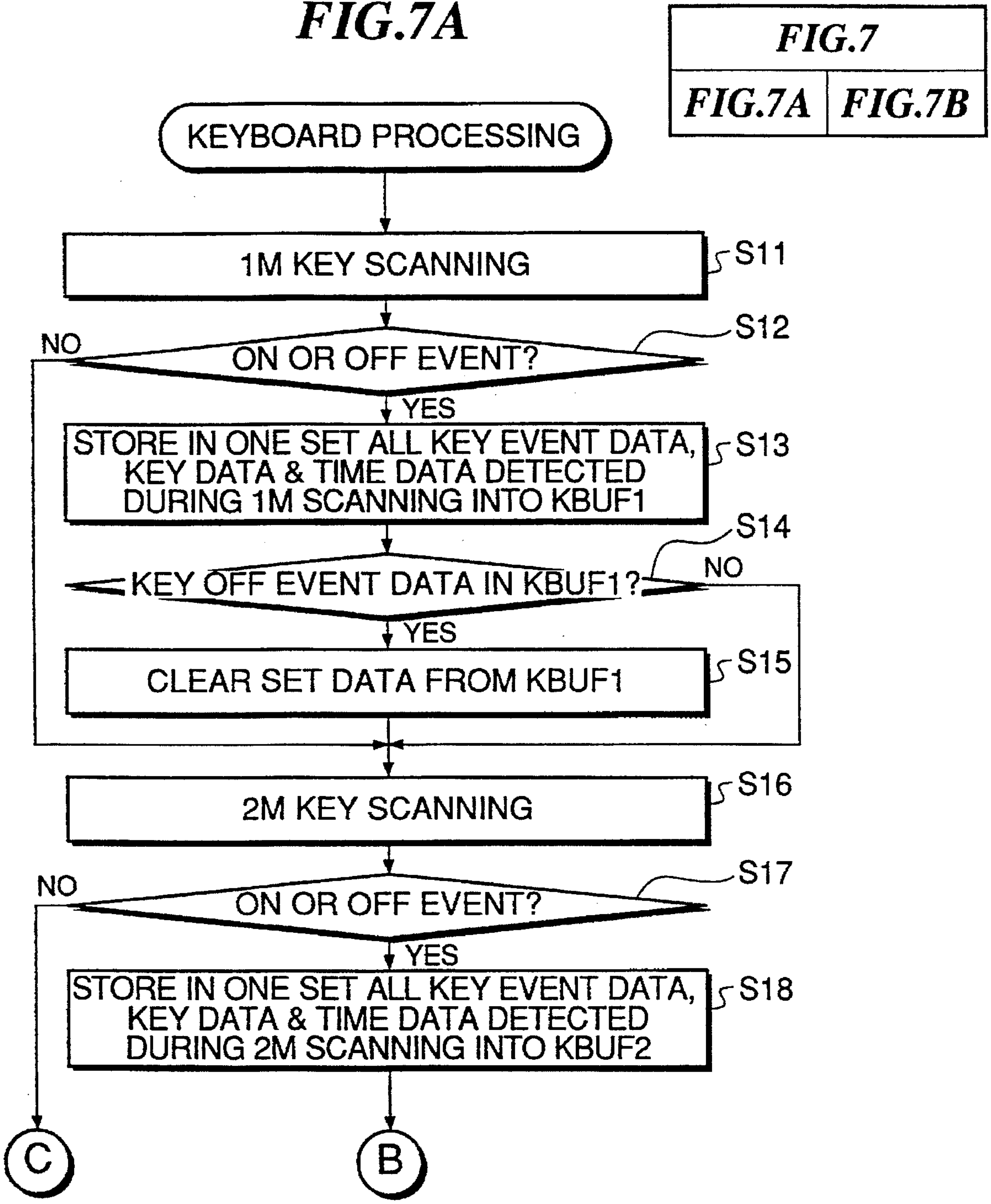
FIG. 7A is a flow chart showing a subroutine for keyboard processing executed at a step S2 in FIG. 6.
Figure 7B:
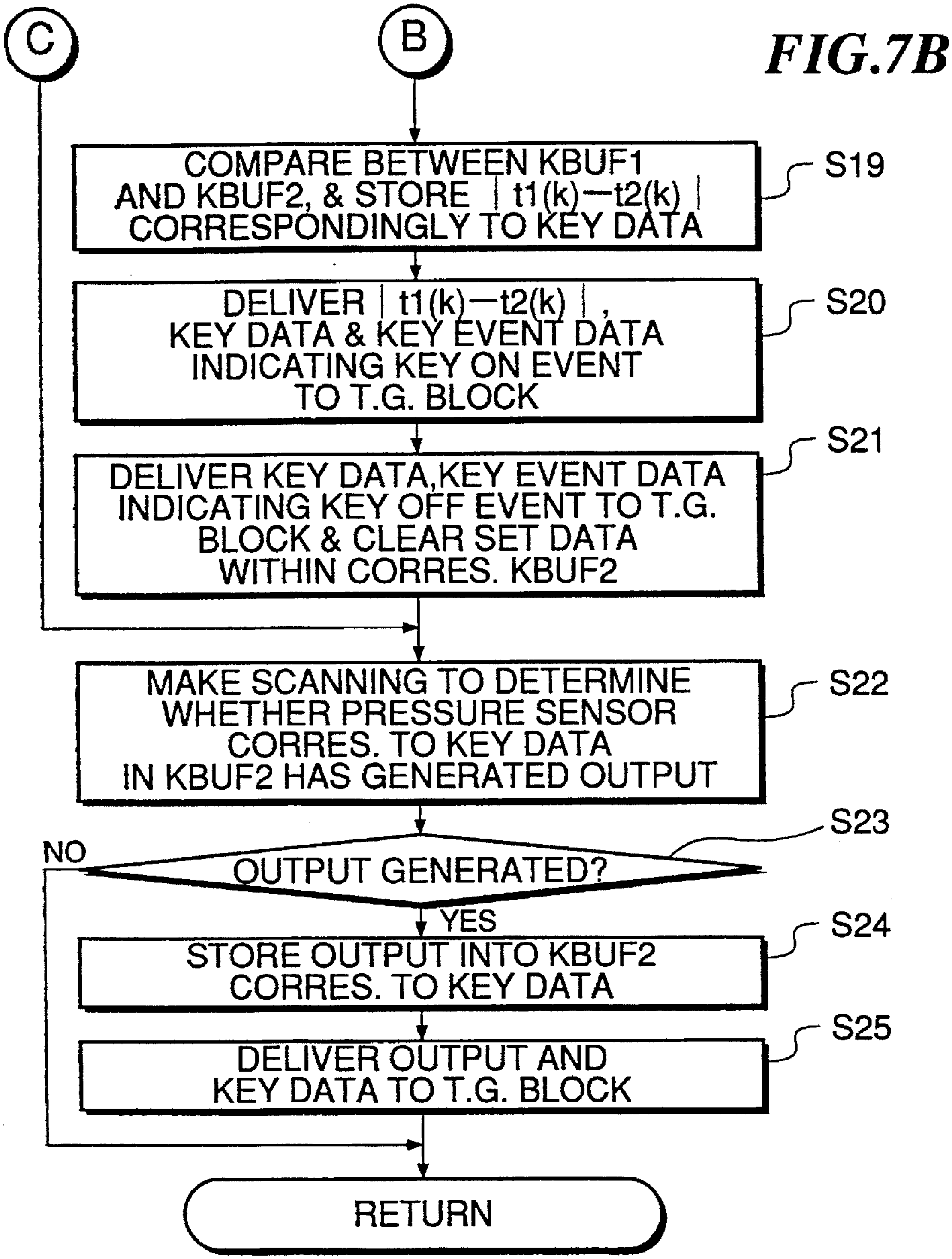
FIG. 7B is a continued part of the FIG. 7A flowchart.

FIG. 7 shows a flowchart of details of a subroutine for the keyboard processing executed at the step S2.

First, key scanning is carried out, based on the status of the 1-make type switch 8*a*, at a step S11, to determine whether or not a key on/off event has occurred, at a step S12. If there has occurred a key on or off event, all the key event data, key data and time data which have been detected during the key scanning are stored in one set into a key buffer KBUF1 preset in a predetermined area within the RAM 233, at a step S13. Here, the key event data indicates occurrence of a key on event when set to "1", and occurrence of a key off event when set to "0". The key data indicates a key code, and the time data is data read out from the aforementioned free-run counter.

Figures 8, 9:
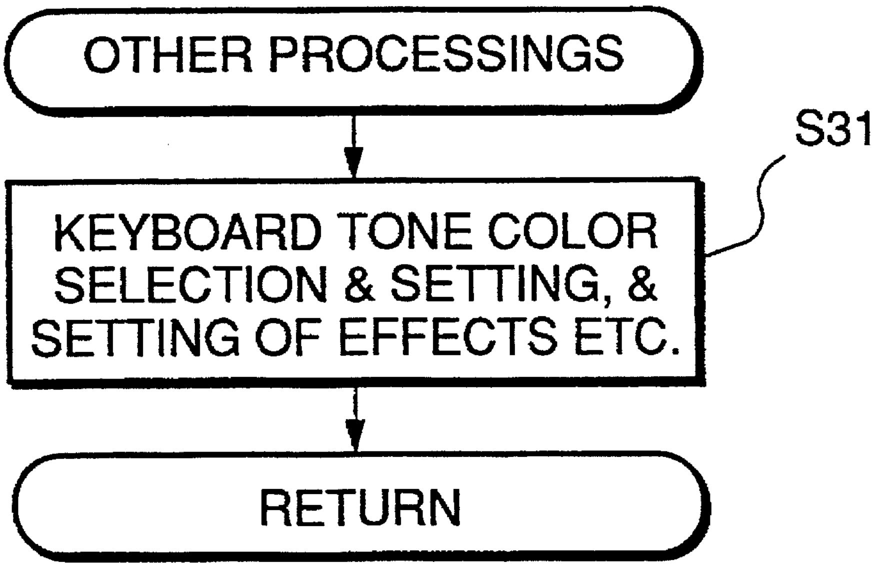
FIG. 8 is a flowchart showing details of a subroutine for other processings executed at a step S3 in FIG. 6.
FIG. 9 is a diagram showing part of a memory map in a key buffer KBUFI.

FIG. 9 shows an example of a memory map stored in the key buffer KBUF1. As shown in the figure, key data, key event data and time data t1(k)(k=1 . . . ) are stored in a manner corresponding to depression and release of the key. As mentioned before, the key event data indicates occurrence of a key on event when set to "1", and occurrence of a key off event when set to "0" In the key buffer KBUF1, key data KD1, KD2 corresponding to key on events and key data KD3 corresponding to a key off event are stored together with respective time data, in a manner corresponding to the key event data.

Referring again to the flowchart of FIG. 7, key event data in the key buffer KBUF1 is retrieved to determine whether or not there has occurred a key off event, that is, whether or not there is any key event data which is set to "0", at a step S14. If there is such key event data, the set of data in the key buffer KBUF1 is cleared at a step S15, whereas if there is no such key event data, the program skips the step S15 over to a step S16.

On the other hand, if it is determined at the step S12 that there has occurred no key on/off event, the program skips the steps S13 to S15 over to the step S16.

At the step S16, key scanning is carried out, based on the status of the 2-make type switch 8*b*, similarly to the step S11, followed by determining at a step S17 whether or not there has occurred a key on or off event. If there has occurred such an event, all the key event data, key data and time data are stored in one set into a key buffer KBUF2 preset in a predetermined area within the RAM $\mathbf{23}_3$, at a step S18.

FIG. 10 shows an example of a memory map stored in the key buffer KBUF2. As shown in the figure, similarly to the key buffer KBUF1 in FIG. 9, key data, key event data and time data t2(k)(k=1 . . . ) are stored in a manner corresponding to depression and release of the key. Further, time difference data and data on the output value from the pressure sensor 16 corresponding to the key data are stored in areas preset in the key buffer KBUF2.

Referring again to the flowchart of FIG. 7, a comparison is made between the data in the key buffer KBUF1 and the data in the key buffer KBUF2. If the two buffers store identical key data and the key event data in the two buffers indicate occurrence of a key on event, time difference data, i.e. the absolute value |t1(k)–t2(k)| of the difference between the time data t1(k) and the time data t2(k) is stored in a manner corresponding to the key data, at a step S19.

Then, if the key event data indicates occurrence of a key on event, the absolute value |t1(k)–t2(k)| obtained at the step S19, the key data and the key event data indicating the key on event are delivered to the tone generation block 24, at a step S20, whereas if the key event data indicates occurrence of a key off event, the key data and the key event data indicating the key off event are delivered to the tone generation block 24, and the set of data in the key buffer KBUF2 corresponding to the key-off event-indicating key event data is cleared at a step S21.

On the other hand, if it is determined at the step S17 that there has occurred no key on or off event, the program skips the steps S18 to S21 over to a step S22.

At the step S22, scanning is made of outputs from the pressure sensors 16 to determine whether or not a pressure sensor corresponding to the key data stored in the key buffer KBUF2 has generated an output at a step S23.

If it is determined at the step S23 that the pressure sensor 16 has generated an output, the output is stored into an area in the key buffer KBUF2 corresponding to the above-mentioned key data at a step S24, and the output and the key data are delivered to the tone generation block 24 at a step S25, followed by terminating the program.

If it is determined at the step S23 that no output has been generated from the pressure sensor 16, the program skips the steps S24 and S25, followed by terminating the program.

FIG. 8 shows details of a subroutine for other processings executed at the step S3. In the subroutine, selecting and setting of the tone color of the keyboard, setting of effects and other factors, etc. are carried out at a step S31.

According to the above described keyboard processing, for example, when the player depresses a key, data corresponding to the depressed key are stored into the key buffer KBUF1 in response to the depression of the key, and then similar data to that stored into the key buffer KBUF1 are stored into the key buffer KBUF2. Time difference data is calculated, and the calculated data is stored into the key buffer KBUF2 together with the output value from the pressure sensor 16. Then, the key data, key event data, time difference data, and the pressure sensor output value stored in the key buffer KBUF2 are delivered to the tone generation block 24. In the tone generation block 24, the key data and key event data delivered thereto are delivered to the tone generation unit $\mathbf{24}_3$ as they are, while the time difference data is delivered to the t-v conversion table $\mathbf{24}_1$ to be converted into the key depression velocity signal Ve1, which is input to the table TBL(v,p) $\mathbf{24}_2$.

Also the output value Pr from the pressure sensor 16 is input to the table TBL(v,p) $\mathbf{24}_2$. As mentioned before, the key depression velocity signal Ve1 and the output value Pr from the pressure sensor 16 are converted into the table output value Drange from the table TBL(v,p) $\mathbf{24}_2$ representing the dynamic range of a musical tone to be generated, which is delivered to the tone generation unit $24_3$. The tone generation unit $24_3$ generates a musical tone signal in response to the key data and key event data and the table output value Drange, which is supplied to the sound system 25 to be generated as a musical tone.

On the other hand, when the depressed key is released by the player, the set of data is cleared from the key buffer KBUF1 in response to the release of the key, and then the corresponding key data and key event data indicating the key off event from the key buffer KBUF2 are delivered to the tone generation block 24, i.e. the tone generation unit $24_3$ to stop generation of the musical tone signal, followed by clearing the set of data.

As described above, according to the present embodiment, the value of the output Drange to be delivered to the tone generation unit $24_3$ is determined based on the key depression velocity and the output from the pressure sensor, which makes it possible to generate a musical tone signal having a wide dynamic range.

Although in the present embodiment the key off processing timing is set equal to the timing of execution of the 2-make type switch status processing as shown by the step S21, alternatively it may be set equal to the timing of execution of the 1-make type switch status processing.

Further, although in the present embodiment the key depression velocity is determined based from the data on the time difference between the contact times of the 1-make type switch and the 2-make type switch, alternatively the key depression velocity may be determined based on time difference data determined from arbitrary two points (except the most depressed point) on the whole stroke of the key sensed by a photo coupler or the like.

Next, another embodiment of the invention will be described.

This embodiment is distinguished from the above described embodiment in that a plurality of kinds of information are delivered to the tone generation unit $24_3$, each kind of information being controlled in dependence on the key depression strength (velocity), and tables to be used for generation of the output Drange are selected according to the key depression strength. More specifically, when the key depression strength is smaller than a predetermined value, e.g. "mf (mezzo forte)", the key depression strength can be accurately calculated from data of time difference between contact times of the 1-make type switch and the 2-make type switch, and therefore the t-v conversion table $24_1$ alone is selected and used, whereas when the key depression strength exceeds the predetermined value, the key depression strength cannot be accurately calculated from the time difference data, and therefore the t-v conversion table $24_1$ and the table TBL(v,p) $24_2$ are used, similarly to the previous embodiment.

In the present embodiment, the t-v conversion table $24_1$ and the table TBL(v,p) $24_2$ are stored in predetermined areas within the RAM $23_3$, and by using these tables, the CPU $23_1$, similarly to the previous embodiment, generates a signal indicative of the dynamic range Drange (in the present embodiment, hereinafter referred to as "the control signal cont") from data stored in the key buffers KBUF1, KBUF2 and delivers the same to the tone generation unit $24_3$.

Figure 11:
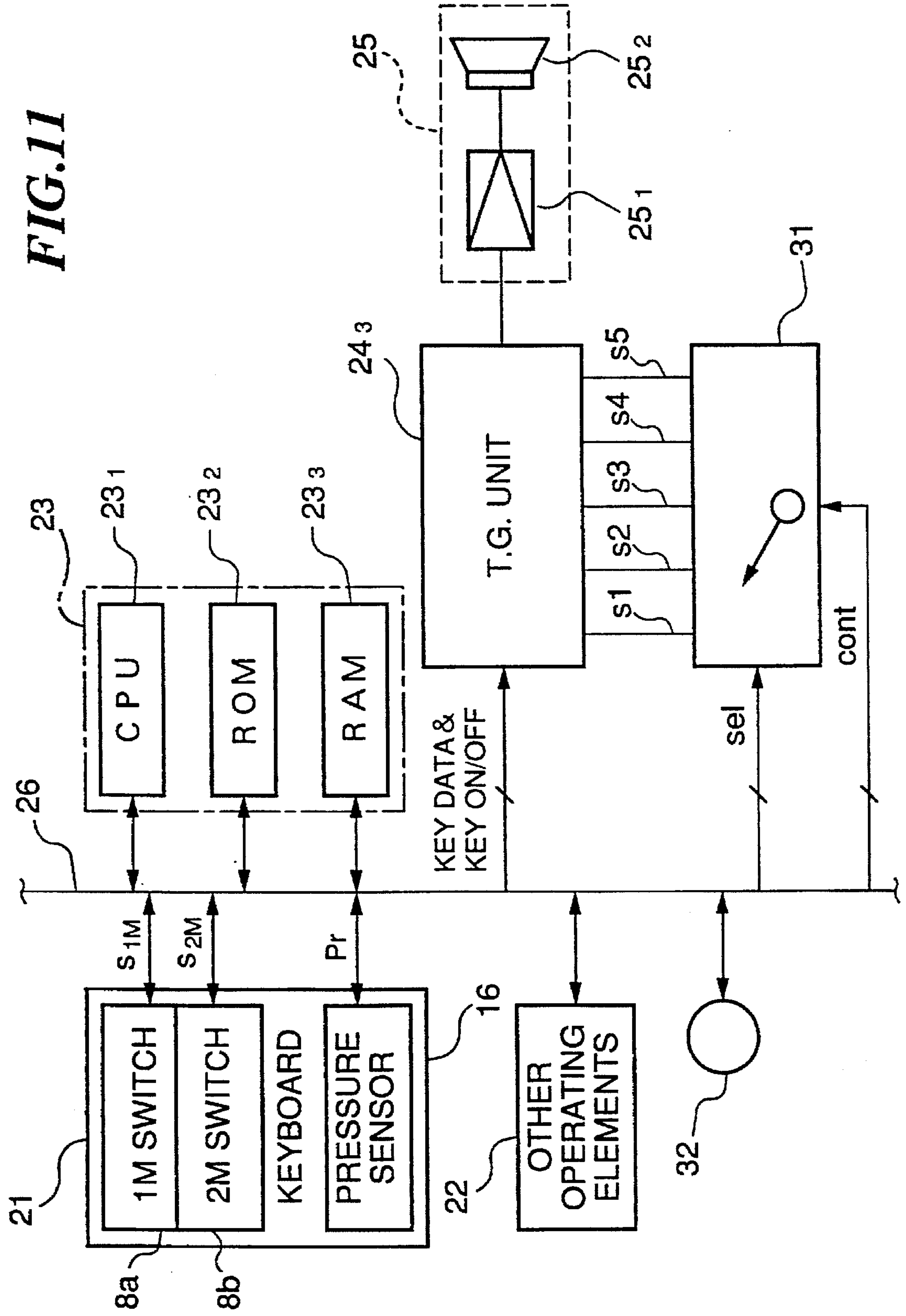
FIG. 11 is a block diagram showing the electronic system arrangement of an electronic musical instrument according to a further embodiment of the invention.

FIG. 11 schematically shows the electronic system arrangement of the present embodiment, in which elements and parts corresponding to those in FIG. 2 are designated by identical reference numerals, description of which is omitted.

In the figure, the tone generation unit $24_3$ is supplied with key data and a key on/off signal similarly to the previous embodiment, and further supplied with signals s1 to s5 for controlling volume, tone color, and effects 1 to 3, respectively, from a selector 31. The selector 31 is supplied via the bus with a signal sel for selecting which of the signals s1 to s5 to be delivered to the tone generation unit 243, as well as the control signal cont. The effects 1 to 3 include reverberation, pitch modulation, vibrato, etc., but may include any other effect which can be controlled according to the key depression strength.

Connected to the bus 26 is a dial operating element 32 for setting information (controlling object) to be controlled in response to key depression (key touch data).

Control processing executed by the CPU 231 of the electronic musical instrument according to the embodiment constructed as above will be described with reference to FIGS. 12 to 14. Also in this embodiment, the main routine of FIG. 6 can be applied, description of which is omitted.

Figure 12:
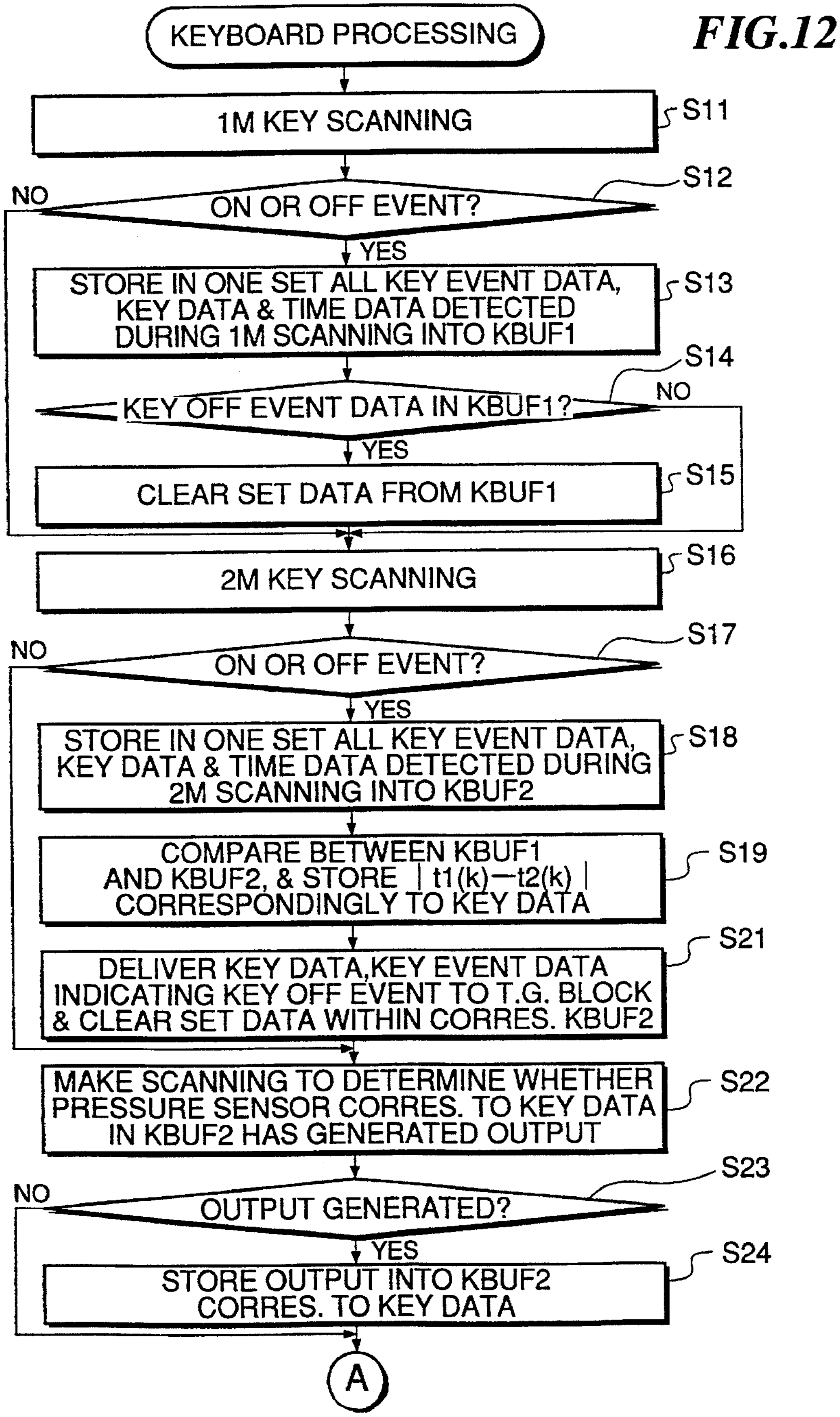
FIG. 12 is a flowchart showing details of a subroutine for keyboard processing executed at the step S2 in FIG. 6.
Figure 13:
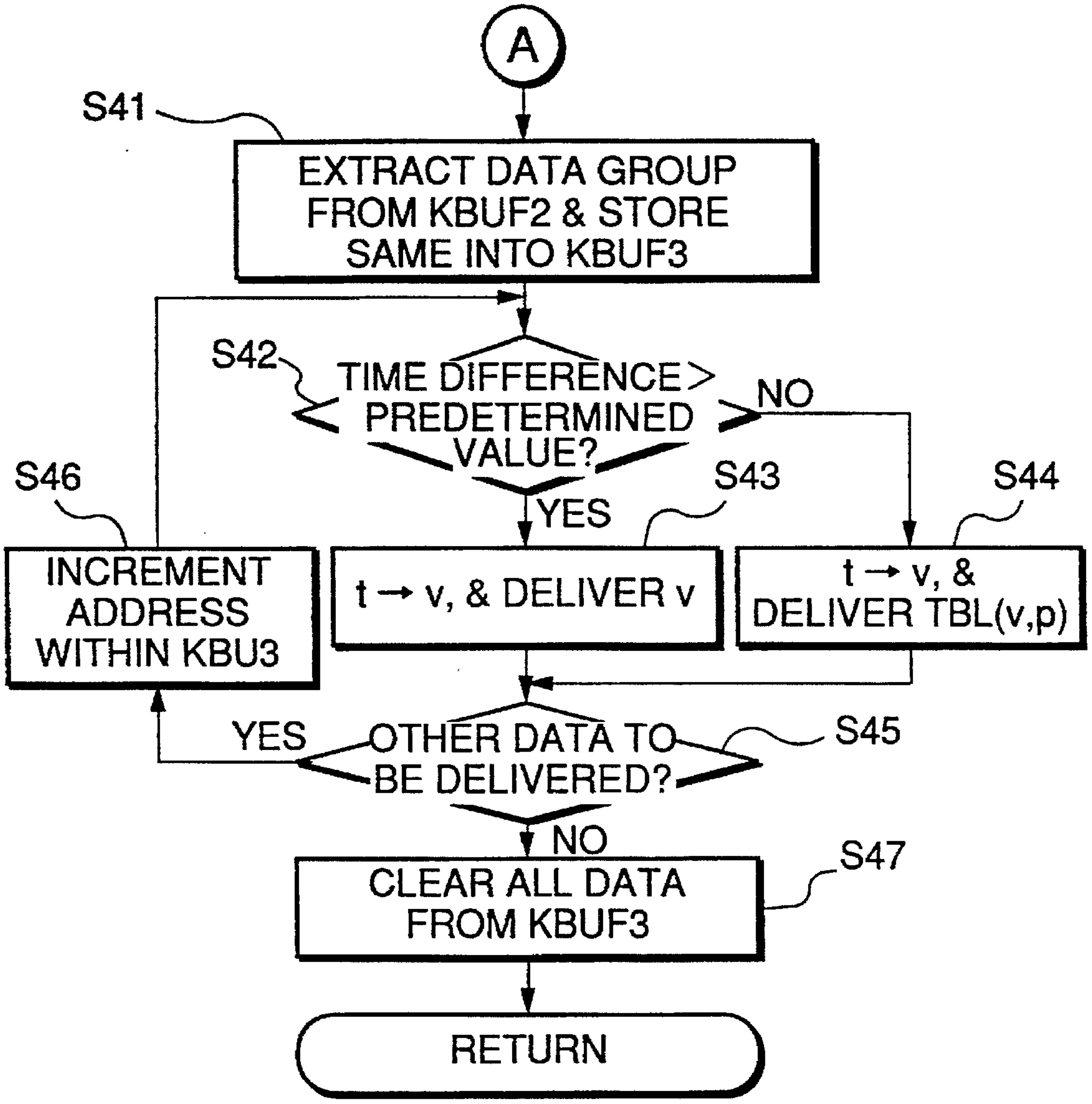
FIG. 13 is a flowchart showing a continued part of the subroutine of FIG. 12.

FIGS. 12 and 13 show details of a subroutine for the keyboard processing executed at the step in FIG. 6, which is different from the keyboard processing subroutine in FIG. 7. In FIG. 12, almost all the steps (steps S11 to S19, and steps S21 to S24) are identical with the steps in FIG. 7, and therefore designated by identical step numbers, description of which is omitted.

At a step S41 in FIG. 13, a group of key data within the key buffer KBUF2 (all corresponding sets of data) corresponding to the key on event detected based on the status of the 2-make switch 8b are extracted from the key buffer KBUF2 and stored into a key buffer KBUF3 preset in a predetermined area in the RAM $23_3$. Then, a comparison is made between a time difference of time difference data corresponding to key data at the first address and a predetermined value, at a step S42. If the time difference is larger than the predetermined value, that is, if the key depression velocity is smaller than a predetermined value (e.g. the aforementioned "mf"), the t-v conversion table is used to determine the key depression velocity from the time difference data, and the determined key depression velocity v is delivered as control data cont through the selector 31 to the tone generation unit $24_3$, at a step S43. On the other hand, if the time difference is smaller than the predetermined value, that is, if the key depression velocity exceeds the predetermined value, similarly to the previous embodiment, the key depression velocity v is determined from the t-v conversion table and the data Drange is determined from the table TBL(v,p) based on the determined key depression velocity v and the output value Pr from the pressure sensor 16, and the determined data Drange is delivered via the selector 31 to the tone generation unit $24_3$, at a step S44.

At the following step S45, it is determined whether or not there remains in the key buffer KBUF3 key data to be delivered to the tone generation unit $24_3$. If there remains such data, an address indicating extracted data stored in the key buffer KBUF3 is incremented by 1 at a step S46, followed by the program returning to the step S42 to repeatedly execute the steps S42 to S44 until data to be delivered becomes no longer stored in the key buffer KBUF3, whereas if no key data to be delivered remains stored in the key buffer KBUF3, all the contents of the key buffer KBUF3 are cleared at a step S47, followed by terminating the program.

In the present embodiment, the determination of the step S42 as to whether or not the key depression velocity is smaller than the predetermined value is made with respect to all the signals s1 to s5 output from the selector 31, and depending upon results of the determination tables to be used are changed. However, in the case of signals not requiring large dynamic ranges, for example, the tone color signal $s_2$, and the effect signals s3 to s5, the above determination need not be carried out, but only the t-v conversion table may be used to convert time difference data to key depression velocity v, and deliver the same to the tone generation unit $\mathbf{24_3}$. In this alternative case, only the conversion by the use of the t-v conversion table is needed with respect to signals other than the volume signal s1, which further simplifies the procedure, as well as saves the memory area by dispensing with the use of the table TBL(v,p).

Figure 14:
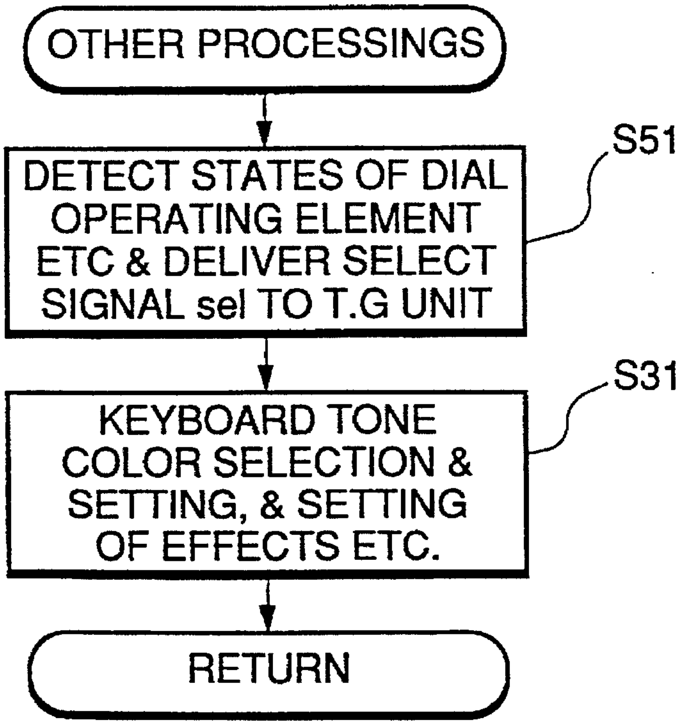
FIG. 14 is a flowchart showing details of a subroutine for other processings executed at the step S3 in FIG. 6.

FIG. 14 shows details of a subroutine for other processings executed at the step S3 in FIG. 6. In the subroutine, a processing using the dial operating element 32 is additionally provided to the other processing subroutine of FIG. 8. In FIG. 14, the step corresponding to the step in FIG. 8 is designated by an identical step number, description of which is omitted.

First, at a step S51, operative states of the dial operating element 32 for setting the controlling object to be controlled in response to key touch data, as well as other operating elements are detected, results of which are delivered to the tone generation unit $\mathbf{24_3}$, followed by executing other setting processings at the step S31, and termination of the program.

As described above, according to the present embodiment, as data to be delivered to the tone generation unit $\mathbf{24_3}$, data of key depression velocity v converted from time difference data by means of the t-v conversion table is used when the key depression strength is smaller than a predetermined value, whereas data of table output value converted by means of the table TBL(v,p) from key depression velocity v converted by means of the t-v conversion table and the output Pr from the pressure sensor is used, similarly to the previous embodiment, when the key depression strength exceeds the predetermined value. Since the latter data is used only when it is difficult to accurately detect the key depression strength, the control procedure can be simplified and accordingly the operation speed can be increased.

In the above described embodiments, initial touch information-determining means determines initial touch information with reference to a table as shown in FIG. 5 (*b*), based on key depression velocity information detected by key depression velocity-detecting means and force information detected by force detecting means. However, the key depression velocity information and the force information may be determined by calculations, to obtain equivalent output to that obtained from the above table.

What is claimed is:

1. An electronic musical apparatus comprising:

a plurality of keys;

a support member supporting said keys, said keys being displaceable relative to said support member in response to depression thereof;

key depression velocity-detecting means for detecting velocity of depression of each of said keys from displacement of said each key caused by depression thereof;

a stationary member;

force detecting means for detecting a pressure force or an impact force with which said each key urgingly contacts said stationary member at or near termination of depression of said each key; and initial touch information-determining means responsive to both the velocity of depression detected by said key depression velocity-detecting means and the pressure force or the impact force detected by said force detecting means, for determining an initial key touch information value for a musical tone to be generated or at least one musical tone parameter, and for controlling said musical tone to be generated, based on the determined initial key touch information value.

2. An electronic musical instrument as claimed in claim 1, wherein said stationary member is said support member.

3. An electronic musical apparatus comprising:

a plurality of keys;

a support member supporting said keys, said keys being displaceable relative to said support member in response to depression thereof;

key depression velocity-detecting means for detecting velocity of depression of each of said keys from displacement of said each key caused by depression thereof;

a moving member being movable in unison with said each key in response to depression thereof;

a stationary member;

force detecting means for detecting a pressure force or an impact force with which said moving member urgingly contacts said stationary member at or near termination of depression of said each key; and initial touch information-determining means responsive to both the velocity of depression detected by said key depression velocity-detecting means and the pressure force or the impact force detected by said force detecting means, for determining an initial key touch information value for a musical tone to be generated or at least one musical tone parameter, and for controlling said musical tone to be generated, based on the determined initial key touch information value.

4. An electronic musical instrument as claimed in claim 3, wherein said moving member is a mass element having a predetermined amount of mass.

5. An electronic musical instrument as claimed in claim 3, wherein said stationary member is said support member.

6. An electronic musical instrument as claimed in claim 3, wherein said initial touch information-determining means controls said musical tone to be generated or said at least one musical tone parameter according to the velocity of depression detected by said depression velocity-detecting means if the detected velocity of depression is below a predetermined value, said initial touch information-determining means determining the initial touch information for said musical tone to be generated or said at least one musical tone parameter according to the detected velocity of depression and the force detected by said force detecting means.

* * * * *